United States Patent [19]

Okuda et al.

[11] 4,099,045
[45] Jul. 4, 1978

[54] ULTRASONIC TESTING METHOD AND APPARATUS FOR RESISTANCE WELDING

[75] Inventors: Takio Okuda; Mikio Inada, both of Amagasaki, Japan

[73] Assignee: Mitsubishi Denki Kabushiki Kaisha, Tokyo, Japan

[21] Appl. No.: 745,915

[22] Filed: Nov. 29, 1976

[30] Foreign Application Priority Data

Dec. 8, 1975 [JP] Japan ................................ 50-146058

[51] Int. Cl.² ............................................. B23K 11/00
[52] U.S. Cl. ........................................ 219/109; 73/629
[58] Field of Search ....................... 219/108, 109, 110; 73/67.7, 67.8 R

[56] References Cited

U.S. PATENT DOCUMENTS

| | | | |
|---|---|---|---|
| 2,433,963 | 1/1948 | Tarbox et al. | 219/109 |
| 3,384,733 | 5/1968 | Burbank et al. | 219/109 |
| 3,410,983 | 11/1968 | Deutsch et al. | 219/109 |
| 3,726,130 | 4/1973 | Hurlebaus | 219/109 |
| 3,813,926 | 6/1974 | Stubbeman | 73/67.7 |

*Primary Examiner*—J. V. Truhe
*Assistant Examiner*—Clifford C. Shaw

[57] ABSTRACT

An ultrasonic vibrator disposed on one of two opposed electrodes having two metallic plates sandwiched between them for being welded intermittently delivers a pulse-shaped ultrasonic wave to a reflecting surface located in the other electrode and receives the wave reflected from the reflecting surface. The vibrator converts the received wave to an electrical signal that is applied to a minimum sensor and a peak sensor. The minimum sensor senses and holds the minimum peak magnitude of the signal which is then subtracted from the peak magnitude of a similar signal developed within the peak sensor at the time of termination of the welding current. The resulting difference between the two magnitudes determines the weld condition of the welded plates.

5 Claims, 5 Drawing Figures

ULTRASONIC TESTING METHOD AND APPARATUS FOR RESISTANCE WELDING

BACKGROUND OF THE INVENTION

This invention relates to an in-process nondestructive testing method utilizing an ultrasonic wave to test welds formed by resistance welding techniques, and to an apparatus for carrying out the same.

Heretofore, the nondestructive testing of spot welded portions through the use of an ultrasonic reflectoscope has been commonly effected in a testing step carried out separately from the welding steps carried out for forming spot welded portions. When using the ultrasonic reflectoscope, the probe thereof has been placed on the welded portion to be tested, and the state of the weld has been determined by the observation of a corresponding waveform produced by multiple reflections and displayed on a Braun tube connected thereto. This has resulted in the disadvantages that the test consumes a relatively lone period of time and the interpretation may be different for different inspectors because the test is not quantitative.

Also among conventional methods of effecting nondestructive test of welded members by the use of an ultrasonic wave and in an in-process manner or during the welding operation, there is known what is called a transmission method. According to this transmission method, a transmitting ultrasonic vibrator is secured to one of a pair of electrodes having sandwiched therebetween members being welded and a receiving ultrasonic vibrator is secured to the other electrode, so that an ultrasonic wave from the transmitting vibrator is transmitted to the receiving vibrator through the members undergoing welding. Then a Braun tube is used to observe any change in the amount of transmission of the ultrasonic wave. The transmission method has brought about a great reduction in testing time and a large increase in testing reliability but it has been disadvantageous because of the necessity of using both transmitting and receiving vibrators.

Further vibrator reflection methods are known which use transmitting and receiving ultrasonic vibrator mounted on one of a pair of electrodes having sandwiched therebetween members being welded to effect a nondestructive test by the utilization of the phenomenon of reflection. These reflection methods are disadvantageous in that the condition of the weld is determined with a very low accuracy because of the utilization of the ultrasonic wave reflected from either the end of surface of that electrode having the vibrator secured thereto or from an interface between such an electrode and the adjacent member being welded.

It is an object of the present invention to provide a new and improved nondestructive testing method for determining the condition of the weld between of members being welded with a high accuracy during the welding operation by using a single ultrasonic vibrator serving as both a transmitter and a receiver.

It is another object of the present invention to provide an apparatus for carrying out the testing method as described in the preceding paragraph which has a simple construction.

SUMMARY OF THE INVENTION

The present invention provides nondestructive testing methods for resistance welding of members to be welded sandwiched between a pair of electrodes having a welding current flowing therethrough, comprising the steps of intermittently transmitting a pulse-shaped ultrasonic wave from an ultrasonic vibrator disposed on one of the electrodes and toward the other electrode, reflecting the ultrasonic wave from a reflecting surface located within the other electrode, sensing the reflected ultrasonic wave by the ultrasonic vibrator and determining the condition of the weld of the welded members by a change in the peak magnitude of the sensed wave.

Preferably, the step of determining the condition of the weld includes sensing a minimum to which the peak magnitude of the sensed ultrasonic wave decreases following an increase in the peak magnitude thereof after the supply of the welding current to the electrodes, sensing the peak magnitude of the sensed ultrasonic wave as it increases after the occurrence of the minimum peak magnitude of the sensed ultrasonic wave, subtracting the minimum peak magnitude from the increased peak magnitude of the sensed ultrasonic wave to estimate the dimension of a nugget formed in the welded members, and determining the condition of the weld by the estimated dimension of the nugget.

The present invention also provides a nondestructive testing apparatus for resistance welding comprising, in combination, a pair of first and second electrodes disposed in opposed relationship on opposite sides of members to be welded and having a welding current flowing therethrough, an ultrasonic vibrator disposed on the first electrode, a transmitter circuit for intermittently driving the ultrasonic vibrator to intermittently transmit a pulse-shaped ultrasonic wave toward the second electrode from the first electrode, a reflecting surface located within the second electrode to reflect the ultrasonic wave transmitted thereto toward the ultrasonic vibrator, a receiver circuit for detecting the peak magnitude of the reflected ultrasonic wave through the ultrasonic vibrator, a gating circuit connected to both the transmitter and the receiver circuits to cause the receiver circuit to deliver only the detected peak magnitude of the reflected wave, a minimum sensor circuit connected to the receiver circuit to sense and hold the minimum peak magnitude of the output from the receiver circuit, a peak sensor circuit for sensing the peak magnitude of the output from the receiver circuit, a comparator circuit for comparing the output from the peak sensor circuit with the output from the minimum sensor circuit to produce an output representative of the difference between the two outputs, and display means for displaying the output from the comparator circuit, the condition of the weld of the welded members being determined by a magnitude of the output displayed on the display means.

Preferably alarm means is connected to the comparator circuit to be energized in response to an output from the comparator circuit which is no higher than a predetermined magnitude.

BRIEF DESCRIPTION OF THE DRAWINGS

The present invention will become more readily apparent from the following detailed description taken in conjunction with the accompanying drawings in which.

DESCRIPTION OF THE PREFERRED EMBODIMENT

For a better understanding of the nature of the present invention, a description will now be made in conjunction with the result of experiments conducted to determine the change in peak magnitude of a reflected ultrasonic wave during the time for which welding is carried out.

Figure 1:
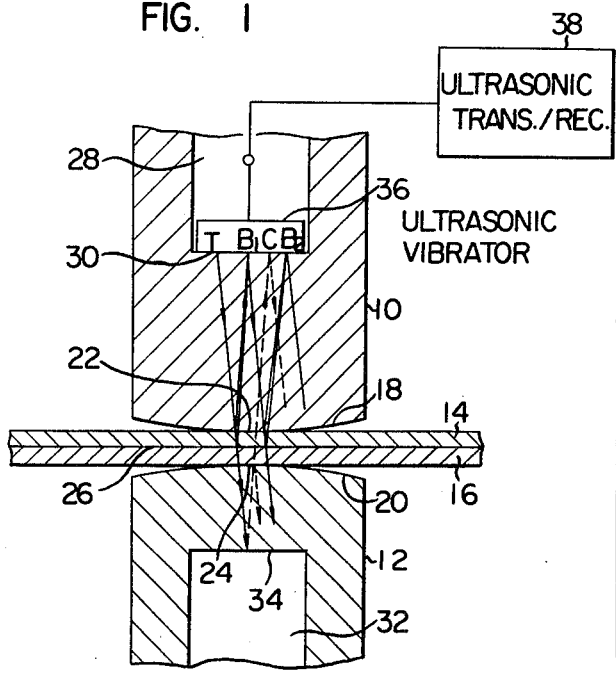
FIG. 1 is a fragmental longitudinal sectional view of the essential portion of a welding apparatus embodying the principles of the present invention and useful in explaining the operation thereof.

Referring now to FIG. 1 of the drawings, there is illustrated the essential portions of a welding apparatus embodying the principles of the present invention. The arrangement illustrated comprises a pair of first and second cylindrical electrodes 10 and 12 respectively disposed in vertically opposed relationship with a pair of plain metallic members 14 and 16 to be welded superposing each other and positioned between the electrodes 10 and 12.

The electrodes 10 and 12 have opposed end surfaces 18 and 20 in the form of spherical segments and contact the members 14 and 16 on contact surfaces 22 and 24 respectively with the members 14 and 16 being maintained in intimate contact with each other along a contact surface or an interface 26.

The first or upper electrode 10 has an internal hollow portion 28 extending along the longitudinal axis thereof and terminating in a flat bottom surface 30 substantially perpendicular to the longitudinal axis of the electrode 10 and located a predetermined distance from the contact surface 18. Similarly the second or lower electrode 12 has an internal hollow portion 32 extending along the longitudinal axis thereof and terminating at a flat bottom surface 34 substantially perpendicular to the longitudinal axis of the electrode 12 and located at a predetermined distance from the contact surface 20. The surface 34 serves as a reflecting surface for an ultrasonic wave as will be apparent from the description given hereinafter.

An ultrasonic vibrator 36 serving as both an ultrasonic transmitting element and an ultrasonic receiving element is fixedly secured to the bottom surface 30 within the hollow portion 28 of the upper electrode 10 and is connected to an ultrasonic transmitter and receiver device 38.

In operation, the transmitter and receiver device 38 intermittently drives the ultrasonic vibrator 38 to intermittently produce an ultrasonic wave in the form of a pulse from the vibrator 36. The ultrasonic wave from the vibrator 36 is transmitted toward the bottom surface 34 in the lower electrode 12 through the end portions of the two electrodes and both members being welded to each other. Then the ultrasonic wave is reflected from various reflecting surfaces located between the bottom surfaces 30 and 34 of the upper and lower hollow electrode portions 28 and 32 respectively. The reflected waves are returned to the ultrasonic vibrator 36 where they are converted to corresponding electrical signals. The electrical signals are sensed by the transmitter and receiver device 38.

Figure 2:
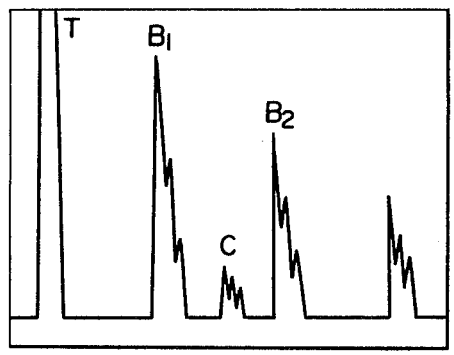
FIG. 2 is the graph illustrating a waveform of reflected ultrasonic waves sensed by the ultrasonic vibrator shown in FIG. 1.

More specifically, as shown in FIG. 2, the ultrasonic vibrator 36 intermittently delivers an ultrasonic wave in the form of a pulse, as a transmitted wave T, toward the electrodes 10 and 12 and the members 14 and 16 being welded. The transmitted wave T is reflected from the contact surfaces 22, 26 and 24 respectively to form a first reflected wave $B_1$, that, in turn, reaches the bottom surface 30 of the upper electrode portion 28. The first reflected wave reaching the bottom surface 30 partly enters the vibrator 36 where it is converted to a corresponding electrical signal while the remaining portion thereof is again reflected from the bottom surface 30 to propagate toward the lower electrode 12. The reflected wave from the bottom surface 30 is reflected from the contact surfaces 22, 26 and 24 and it is combined into a second reflected wave $B_2$ that reaches the bottom surface 30. One part of the second reflected wave $B_2$ enters the ultrasonic vibrator 36 and the remaining part thereof is again reflected from the bottom surface 30 toward the electrode 12 as was the first reflected wave $B_1$ to form succeeding reflected waves.

The transmitted wave, and the first and second reflected waves $B_1$ and $B_2$ are shown in FIG. 1 as traveling along solid lines in the directions indicated by the arrowheads and labelled with the reference characters $T_1$, $B_1$ and $B_2$ respectively. The dotted line labelled with the reference character C in FIG. 1 designates the path along which the transmitted wave T travels after having been transmitted through the contact surfaces 22, 26 and 24 and reflected from the bottom surface 34 of the internal hollow portion 32 in the lower electrode 12 and then to the upper bottom surface 30. This reflected wave C includes one portion entering the ultrasonic vibrator 36 where it is converted to a corresponding electrical signal and the remaining portion is reflected toward the electrode 12 from the bottom surface 30 of the upper electrode 10.

Those electrical signals converted by the ultrasonic vibrator 36 are sensed by the transmitter and receiver device 38 and displayed on a Braun tube (not shown) connected thereto and appear as shown in FIG. 2. The multiple reflection waveform as shown in FIG. 2 includes electrical signals in the form of pulses corresponding to a transmission waveform T, a first reflection waveform $B_1$, a reflection waveform C, a second reflection waveform $B_2$ etc. developed in the named order.

The first reflected wave $B_1$ is formed mainly of the reflected wave from the contact surface 22 between the end surface 18 of the first electrode 10 and the adjacent member 14 being welded to the member 16. From FIG. 2 it is seen that this portion of the first reflected wave $B_1$ is always attenuated the same way. This is because the contact between the end surface 18 of the upper electrode 10 and the adjacent welded member 14 is good and also the contact area therefor increases as the particular welding process proceeds. As seen in FIG. 2, the second reflected wave $B_2$ is attenuated in a way substantially similar to the attenuation of the first reflected wave $B_1$.

On the other hand, the reflected wave C is not always attenuated the same way, as are the reflected waves $B_1$ and $B_2$, because wave C passes through the welded portion twice and therefore the attenuation is affected by changes in properties of the material of the welded members 14 and 16 due to an increase in temperature thereof. It will readily be understood that the ultrasonic vibrator 36 is required to transmit the ultrasonic wave in the form of pulses having a predetermined pulse repetition period sufficient to permit the ultrasonic wave reflected from the reflecting surface 34 to reach the vibrator 36 during time interval between the transmitted pulses.

Figure 3:
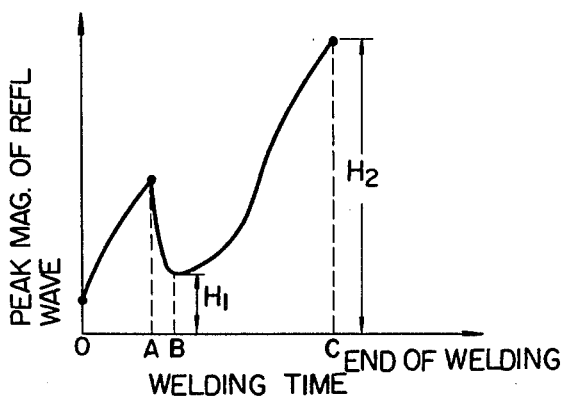
FIG. 3 is a characteristic curve showing the change in peak magnitude of the reflected wave C shown in FIGS. 1 and 2 and serving as an information medium in the present invention.

Referring now to FIG. 3, there is illustrated the peak magnitude of the ultrasonic reflected wave C plotted on the ordinate against the welding time plotted on the abscissa. From FIG. 3 it is seen that, as the welding time passes the peak magnitude of the reflected wave C gradually increases from a time point 0 at which the welding current starts to flow through the electrodes 10 and 12 and the members 14 and 16 to be welded until it reaches a maximum at a time point A. Thereafter the peak magnitude of the reflected wave suddenly decreases to a minimum of $H_1$ at a time point B. As further welding time passes, the peak magnitude of the reflected wave C again gradually increases until it reaches an increased magnitude of $H_2$ at a time point C at which the welding current terminates.

The gradual increase in peak magnitude of the reflected wave C during the time interval from the time point 0 to the time point A results from an increase in temperature of the contact surfaces 22, 26 and 24 and therefore an improvement in the contact thereof with the passage of the welding time.

In order to trace the origin of the sudden decrease in peak magnitude of the reflected wave C during the time interval from the time point A to the time point B, the welded section which has been cut off from the welded members has been metallographically inspected. The result of the inspections indicates that a minute nugget starts to be formed in the members being welded during that portion of the welding process extending over time interval from the time point A to the time point B. From this it is concluded that the change in peak magnitude of the reflected wave C occurring during the time interval from the time point A to the time point B is caused by the abrupt attenuation of the ultrasonic wave occurring when that portion of the metal of the members 14 and 16 undergoing welding located on and adjacent to the contact surface or interface 26 has been transformed from its solid to its liquid phase. Therefore whether or not a nugget is formed in the particular members being welded can be determined by sensing the time point B.

Figure 4:
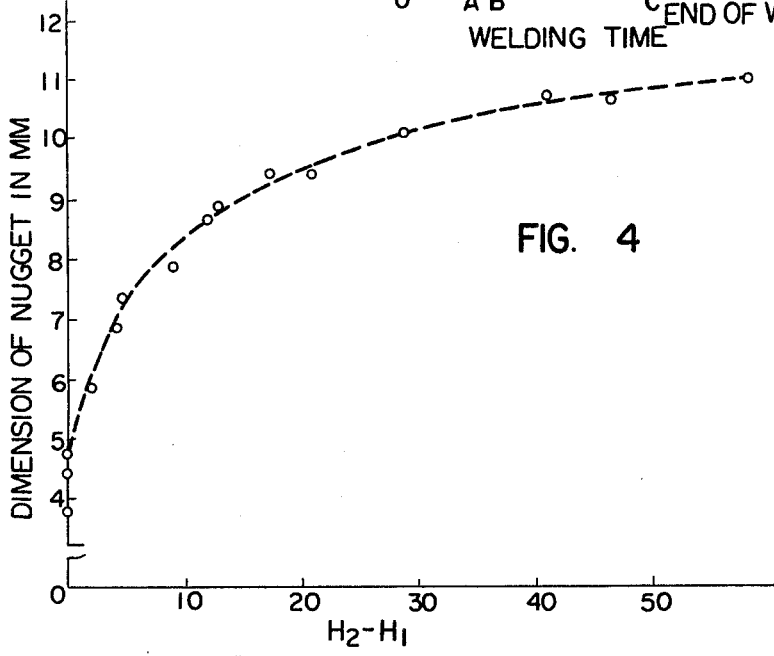
FIG. 4 is a graph illustrating the change in peak magnitude of the reflected ultrasonic wave plotted against the dimension of the nugget formed in the members undergoing welding as shown in FIG. 1.

A plurality of pairs of mild steel plates 3.2 millimeters thick were welded with welding currents of from 15 to 23.5 kiloamperes for welding times of from 16 to 26 cycles of the welding current under pressures of 680, 900, 1150, 1200 and 1500 kilograms. The minimum peak magnitude $H_1$ and the peak magnitude $H_2$ of the reflected ultrasonic wave C developed at the time points B and C respectively and also the dimensions of the nuggets formed in the welded plates were measured in the direction parallel to the surfaces of the plates being welded, i.e. transverse to the direction of the applied ultrasonic waves wherein the ordinate values represent the dimension of a nugget in millimeters and values on the abscissa of a nugget in millimeters and the axis of abscissas represent the difference between the magnitudes $H_2$ and $H_1$. From FIG. 4 it is seen that the dimension of the nugget definitely correlates with the difference between the peak magnitudes $H_2$ and $H_1$. Accordingly, in order to determine the dimension of the nugget formed in a welded portion, the ultrasonic reflected wave C is extracted by using a gating circuit while measuring both the minimum peak magnitude $H_1$ thereof developed at the time point B as above described and the peak magnitude thereof developed at the time point C as above described, that is, when the welding current involved terminates. Then the difference between the measured magnitudes $H_2$ and $H_1$ is found. This method permits the determination of whether the resulting weld is good or poor with high reliability.

Figure 5:
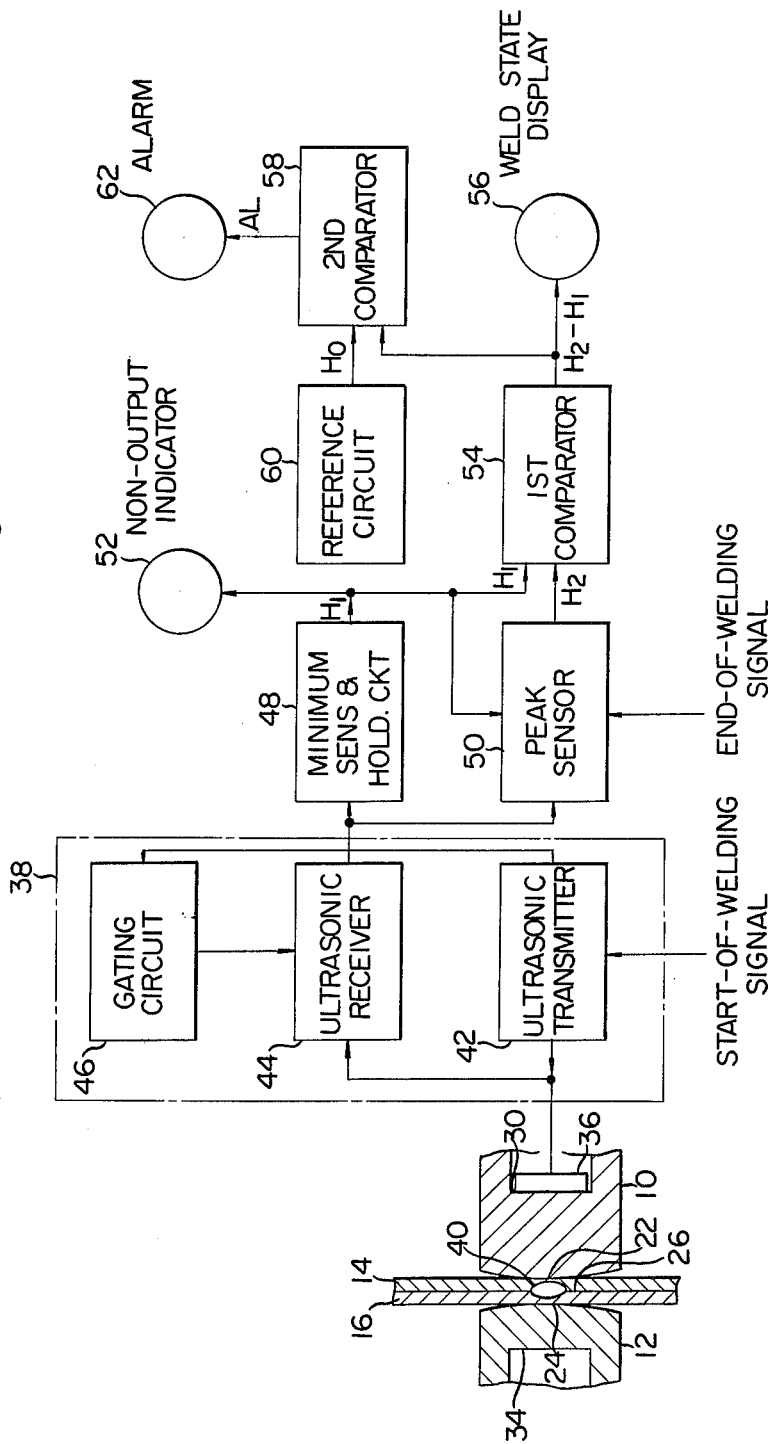
FIG. 5 is a block diagram of a nondestructive testing apparatus constructed in accordance with the principles of the present invention.

The present invention also provides a nondestructive testing apparatus for carrying out the testing method as above described and a preferred embodiment thereof is illustrated in FIG. 5 wherein like reference numerals designate the components identical to those shown in FIG. 1. In FIG. 5, the arrangement of FIG. 1 is shown as having a nugget 40 formed on and adjacent to the interface 26 between a pair of flat metallic members 14 and 16 undergoing welding and positioned between the first and second welding electrodes 10 and 12 respectively and including the transmitter and receiver device 38 formed of an ultrasonic transmitter circuit 42 connected to the ultrasonic vibrator 36, an ultrasonic receiver circuit 44 connected to the vibrator 36 and a gating circuit 46 connected to the transmitter and receiver circuits 42 and 44 respectively. The transmitter circuit 42 is responsive to a start-of-welding signal applied thereto to intermittently apply a voltage to the ultrasonic vibrator 36 to cause the vibrator 36 to deliver an ultrasonic wave in the form of pulses toward the second electrode 12. It is noted that the pulses have a predetermined pulse repetition period as above described. The ultrasonic vibrator 36 receives ultrasonic reflected waves as above described in conjunction with FIG. 1 and converts them to corresponding electrical signals subsequently applied to the ultrasonic receiver circuit 44. The receiver circuit 44 detects the peak magnitude of that electrical signal corresponding to the ultrasonic reflected wave reflected from the reflecting surface 34 within the second electrode 12 and can only deliver it under the control of a timing signal provided by the gating circuit 46. The output from the receiver circuit 44 thus selected by the gating circuit 46 is connected to both a minimum sensing and holding circuit 48 and a peak sensor circuit 50.

The minimum sensing and holding circuit 48 is operative to sense and hold a minimum $H_1$ of the output from the receiver circuit 44 and supply it to a non-output indicator 52, a first comparator 54 and the peak sensor circuit 50. The indicator 52 is adapted to be energized in the absence of an output from the minimum sensing and holding circuit 48 to indicate that the latter 48 has provided no output during the particular welding time. The peak sensor circuit 50 is adapted to have applied thereto an end-of-welding signal as shown in FIG. 5. When supplied with the end-of-welding signal, the peak sensor circuit 50 holds the peak magnitude $H_2$ of the electrical signal received thereby at the time of the reception of the end-of-welding signal and only when it has received the output voltage $H_1$ from the circuit 48.

The output voltage $H_2$ held by the peak sensor circuit 50 is applied to a first comparator circuit 54 where it is compared with the output voltage $H_1$ from the minimum sensing and holding circuit 48. The comparator circuit 54 produces a difference voltage $(H_2 - H_1)$ between the two voltages. The difference voltage from the first comparator circuit 54 is supplied to a weld-state display device 56 so as to be displayed thereon. Thus one can decide the weld condition of the particular welded portion from the reading on the display device 56 as will readily be understood from the graph of FIG. 4.

The difference voltage from the first comparator circuit 54 is also applied to a second comparator circuit 58 where it is compared with a reference voltage $H_o$ provided from a reference circuit 60. The reference voltage $H_o$ provides a measure of the desired dimension of a nugget formed in the welded portion involved. When the difference voltage is smaller than the reference voltage as determined thereby, the second comparator circuit 58 produces an alarm signal AL. The alarm signal AL is delivered to an alarm or an alarm indicator 62 to actuate it.

From the foregoing it will readily be appreciated that in the arrangement of FIG. 5 the time point B at which a nugget has been formed in the particular metallic members being welded is sensed by the minimum sensing and holding circuit 48 and the dimension of the nugget formed in the metallic members being welded between the time point B and a time point C when the welding current terminates is displayed on the weld state display device 56. Also, when energized, the non-output indicator 52 indicates that even a small nugget has not been formed in the particular metallic members being welded, while when the output voltage $(H_2-H_1)$ from the first comparator circuit 54 is less than the reference voltage of $H_o$ corresponding to the desired dimension of a nugget formed in the welded member, the alarm indicator or alarm 62 is put in operation.

The present invention is advantageous over conventional transmission methods using two ultrasonic vibrators or a transmitter and a receiver in that an ultrasonic wave passes through the welded portion twice to increase the difference in the peak magnitude of the reflected ultrasonic wave with respect to the dimension of a nugget formed in the welded portion resulting in a high accuracy in the result of the particular test being obtained with a single ultrasonic vibrator.

While the present invention has been illustrated and described in conjunction with a single preferred embodiment thereof it is to be understood that numerous changes and modifications may be resorted to without departing from the spirit and scope of the present invention. For example, the reference circuit 60, the second comparator circuit 58 and the alarm or indicator 62 may be omitted. This is because the relationship between the dimension of a nugget formed in a pair of metallic members undergoing welding and the difference in peak magnitudes $(H_2-H_1)$ is preliminarily known as above described in conjunction with FIG. 4 and because the dimension of the nugget can be estimated by a reading on the weld state display device 56. If desired, the non-output indicator 52 may also be omitted.

What we claim is:

1. A nondestructive testing method for determining the sufficiency of resistance welding of members welded between a pair of opposed electrodes having a welding current flowing therethrough, comprising the steps of intermittently transmitting a pulse-shaped ultrasonic wave from an ultrasonic vibrator disposed in one of said electrodes toward the other electrode, reflecting said ultrasonic wave from a reflecting surface located within said other electrode, sensing the minimum value of the peak magnitude of said reflected ultrasonic wave following an increase in the peak magnitude thereof after the start of the supply of the welding current to said electrodes, sensing the maximum value of the peak magnitude of said reflected ultrasonic wave during the time interval after the occurrence of said minimum peak magnitude and up to the time of cutoff of the welding current to said electrodes, subtracting said minimum value of the peak magnitude from said maximum value of the peak magnitude for estimating the dimension in the direction transverse to the transmitted ultrasonic wave of a nugget formed in the welded members, whereby the sufficiency of the weld of the welded members can be judged from the estimated dimension of the nugget.

2. A welding and nondestructive testing apparatus for determining the sufficiency of resistance welding of two superposed members being welded comprising, in combination, a pair of first and second electrodes in spaced opposed relationship for welding the members to be welded therebetween, welding current means connected to said electrodes for flowing a welding current through said electrodes, an ultrasonic vibrator disposed in said first electrode for transmitting and receiving ultrasonic vibrations, a transmitter circuit connected to said ultrasonic vibrator for intermittently driving said ultrasonic vibrator to intermittently transmit a pulse-shaped ultrasonic wave toward said second electrode from said ultrasonic vibrator, a reflecting surface located within said second electrode for reflecting said pulse-shaped ultrasonic wave, a receiver circuit connected to said ultrasonic vibrator for detecting the peak magnitude of said reflected ultrasonic wave received through said ultrasonic vibrator, a gating circuit connected to said transmitter circuit and to said receiver circuit for driving said receiver circuit for producing as an output only the detected peak magnitude of said reflected wave, a minimum sensing and holding circuit connected to said receiver circuit for sensing and holding the minimum value of the output from said receiver circuit, a maximum sensing circuit connected to said receiver circuit to sense the maximum value of said output from said receiver circuit, a comparator circuit connected to said minimum sensing and holding circuit and to said maximum sensing circuit for comparing the output from said maximum sensing circuit with the output from said minimum sensing and holding circuit and producing an output representative of the difference between the two outputs, and display means for displaying the output from said comparator circuit, whereby the sufficiency of the weld of said welded members can be judged by the magnitude of the output displayed on said display means.

3. A welding and nondestructive testing apparatus as claimed in claim 2 further comprising alarm means connected to said comparator circuit and energized in response to an output from said comparator circuit no greater than a predetermined magnitude.

4. A welding and nondestructive testing apparatus as claimed in claim 2 further comprising an indicator means connected to said minimum sensing and holding circuit for being energized in the absence of an output from said minimum sensing and holding circuit.

5. A nondestructive testing apparatus for determining the sufficiency of resistance welding of two superposed members being welded comprising, in combination, a pair of first and second members in spaced opposed relationship for permitting the welded members to be positioned between said members, an ultrasonic vibrator disposed in said first member for transmitting and receiving ultrasonic vibrations, a transmitter circuit connected to said ultrasonic vibrator for intermittently driving said ultrasonic vibrator to intermittently transmit a pulse-shaped ultrasonic wave toward said second member from said ultrasonic vibrator, a reflecting surface located within said second member for reflecting said pulse-shaped ultrasonic wave, a receiver circuit connected to said ultrasonic vibrator for detecting the peak magnitude of said reflected ultrasonic wave received through said ultrasonic vibrator, a gating circuit connected to said transmitter circuit and to said receiver circuit for driving said receiver circuit for producing as an output only the detected peak magnitude of said reflected wave, a minimum sensing and holding circuit connected to receiver circuit for sensing and holding the minimum value of the output from said receiver circuit, a maximum sensing circuit connected to said receiver circuit to sense the maximum value of said output from said receiver circuit, a comparator circuit connected to said minimum sensing and holding circuit and to said maximum sensing circuit for comparing the output from said maximum sensing circuit with the output from said minimum sensing and holding circuit and producing an output representative of the difference between the two outputs, and display means for displaying the output from said comparator circuit, whereby the sufficiency of the weld of said welded members can be judged by the magnitude of the output displayed on said display means.

* * * * *